US008338389B2

(12) United States Patent
Suzuki et al.

(10) Patent No.: US 8,338,389 B2
(45) Date of Patent: Dec. 25, 2012

(54) AGENT FOR PREVENTING OR AMELIORATING OBESITY

(75) Inventors: Junko Suzuki, Haga-gun (JP); Akira Shimotoyodome, Haga-gun (JP); Tomohisa Ichiba, Sumida-ku (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 12/817,719

(22) Filed: Jun. 17, 2010

(65) Prior Publication Data
US 2011/0098245 A1 Apr. 28, 2011

(30) Foreign Application Priority Data

Jun. 17, 2009 (JP) ................................ 2009-144577

(51) Int. Cl.
*A01N 43/04* (2006.01)
*A61K 31/70* (2006.01)

(52) U.S. Cl. ......................................... 514/54
(58) Field of Classification Search ........................ None
See application file for complete search history.

(56) References Cited

U.S. PATENT DOCUMENTS

| | | | |
|---|---|---|---|
| 4,348,420 A | 9/1982 | Lynch et al. | |
| 4,673,582 A | 6/1987 | Nofre et al. | |
| 4,877,895 A | 10/1989 | Nofre et al. | |
| 5,034,378 A | 7/1991 | Cox | |
| 5,082,684 A | 1/1992 | Fung | |
| 5,158,798 A | 10/1992 | Fung et al. | |
| 5,273,753 A | 12/1993 | Ishihara et al. | |
| 5,283,076 A | 2/1994 | Kazuyuki et al. | |
| 5,308,639 A | 5/1994 | Fung | |
| 5,460,957 A | 10/1995 | Hiura et al. | |
| 5,516,666 A | 5/1996 | Nozomi et al. | |
| 5,543,168 A * | 8/1996 | Yamasaki et al. | 426/557 |
| 5,609,896 A | 3/1997 | Cox et al. | |
| 5,626,901 A | 5/1997 | Ambjerg Pedersen | |
| 5,641,533 A | 6/1997 | Ambjerg Pedersen | |
| 5,718,920 A | 2/1998 | Notenbomer | |
| 5,770,217 A | 6/1998 | Kutilek, III et al. | |
| 5,922,379 A | 7/1999 | Wang | |
| 6,136,349 A | 10/2000 | Karppanen et al. | |
| 6,171,624 B1 | 1/2001 | Reddy et al. | |
| 6,248,390 B1 | 6/2001 | Stillman | |
| 6,306,449 B1 | 10/2001 | Reddy et al. | |
| 6,379,725 B1 | 4/2002 | Wang et al. | |
| 6,455,083 B1 | 9/2002 | Wang | |
| 6,572,898 B2 | 6/2003 | Nelson et al. | |
| 6,645,536 B2 | 11/2003 | D'Abramo | |
| 6,770,305 B2 | 8/2004 | Nelson et al. | |
| 6,815,433 B2 | 11/2004 | Hansson et al. | |
| 6,815,436 B2 | 11/2004 | Hansson et al. | |
| 6,835,015 B2 | 12/2004 | Pearce | |
| 6,884,445 B2 | 4/2005 | Navarro Y. Koren et al. | |
| 6,905,431 B2 | 6/2005 | Pearce et al. | |
| 6,929,807 B1 | 8/2005 | McAnalley et al. | |
| 7,115,297 B2 | 10/2006 | Stillman | |
| 7,157,431 B2 | 1/2007 | McAnalley et al. | |
| 7,196,064 B2 | 3/2007 | McAnalley et al. | |
| 7,199,104 B2 | 4/2007 | McAnalley et al. | |
| 7,202,220 B2 | 4/2007 | McAnalley et al. | |
| 7,238,380 B2 | 7/2007 | Stillman | |
| 7,550,436 B2 | 6/2009 | Takahashi et al. | |
| 7,666,448 B2 | 2/2010 | Mower | |
| 7,700,144 B2 | 4/2010 | Pandey et al. | |
| 7,722,902 B2 | 5/2010 | Mower | |
| 7,749,545 B2 | 7/2010 | Mower | |
| 7,776,365 B2 | 8/2010 | Mower | |
| 7,838,004 B2 | 11/2010 | Mower | |
| 7,892,586 B2 | 2/2011 | Stillman | |
| 7,972,620 B2 | 7/2011 | Andersen et al. | |
| 8,097,271 B2 | 1/2012 | Lakkis et al. | |
| 8,101,208 B2 | 1/2012 | Lakkis et al. | |
| 2002/0009502 A1 | 1/2002 | Nelson et al. | |
| 2002/0094971 A1 | 7/2002 | Hansson et al. | |
| 2002/0192335 A1 | 12/2002 | D'Abramo | |
| 2003/0004135 A1 | 1/2003 | Hansson et al. | |
| 2003/0064104 A1 | 4/2003 | Stillman | |
| 2003/0072770 A1 | 4/2003 | McAnalley et al. | |
| 2003/0118712 A1 | 6/2003 | Navarro Y Koren et al. | |
| 2003/0144179 A1 | 7/2003 | Takahashi et al. | |
| 2003/0175345 A1 | 9/2003 | Hite et al. | |

(Continued)

FOREIGN PATENT DOCUMENTS

AT A 197375 A 4/1978

(Continued)

OTHER PUBLICATIONS

Database WPI Week 200709, Thompson Scientific, AN 2007-086835./JP 2006-362085, XP002513039, Dec. 21, 2006.*
John H. Cummings, "Nutritional implications of dietary fiber", The American Journal of Clinical Nutrition 31, (10 Suppl), 1978, pp. S21-S29.
Shigeru Wakabayashi, "The Effects of Indigestible Dextrin on Sugar Tolerance: I. Studies on Digestion—Absorption and Sugar Tolerance", Folia Endocrinologica Japonica, 68, 1992, pp. 623-635.
Kay M. Behall, et al., "Diets containing high amylose vs amylopectin starch: effects on metabolic variables in human subjects[1-3]", Am. J. Clin. Nutr., 49, 1989, pp. 337-344.

(Continued)

*Primary Examiner* — Traviss C McIntosh, III
(74) *Attorney, Agent, or Firm* — Oblon, Spivak, McClelland, Maier & Neustadt, L.L.P.

(57) ABSTRACT

The present invention provides a method for preventing or ameliorating obesity, for inhibiting accumulation of visceral fat, for inhibiting accumulation of liver lipid, for preventing or ameliorating fatty liver, including using a material for a pharmaceutical product or food, which has inhibitory actions on body weight increase, accumulation of visceral fat and accumulation of liver lipid. The present invention is also directed to a method for preventing or ameliorating obesity, a method for inhibiting accumulation of visceral fat, a method for inhibiting accumulation of liver lipid, and a method for preventing or ameliorating fatty liver, which methods include administering potassium alginate to a subject in need thereof or having the subject take potassium alginate.

13 Claims, No Drawings

U.S. PATENT DOCUMENTS

| | | |
|---|---|---|
| 2003/0198726 A1 | 10/2003 | Navarro Y. Koren et al. |
| 2003/0203048 A1 | 10/2003 | Nelson et al. |
| 2003/0211201 A1 | 11/2003 | Stillman |
| 2003/0224090 A1 | 12/2003 | Pearce et al. |
| 2003/0235453 A1 | 12/2003 | Pearce |
| 2003/0235662 A1 | 12/2003 | Pearce et al. |
| 2004/0076614 A1 | 4/2004 | Schur |
| 2004/0170706 A1 | 9/2004 | McAnalley et al. |
| 2004/0171583 A1 | 9/2004 | McAnalley et al. |
| 2004/0198699 A1 | 10/2004 | Hansson et al. |
| 2004/0224068 A1 | 11/2004 | Lee |
| 2004/0247746 A1 | 12/2004 | Pearce et al. |
| 2005/0008713 A1 | 1/2005 | McAnalley et al. |
| 2005/0008735 A1 | 1/2005 | Pearce |
| 2005/0013902 A1 | 1/2005 | Pearce |
| 2005/0070502 A1 | 3/2005 | Hansson et al. |
| 2005/0074525 A1 | 4/2005 | Pearce |
| 2005/0074526 A1 | 4/2005 | Pearce |
| 2005/0100639 A1 | 5/2005 | Pearce |
| 2005/0100647 A1 | 5/2005 | Pearce |
| 2005/0100648 A1 | 5/2005 | Pearce |
| 2005/0100651 A1 | 5/2005 | Pearce |
| 2005/0106233 A1 | 5/2005 | Andersen et al. |
| 2005/0118326 A1 | 6/2005 | Anfinsen et al. |
| 2005/0175735 A1 | 8/2005 | Gandhi et al. |
| 2006/0034894 A1 | 2/2006 | Lakkis et al. |
| 2006/0034936 A1 | 2/2006 | Lakkis et al. |
| 2006/0051296 A1 | 3/2006 | Holahan |
| 2006/0193956 A1 | 8/2006 | Leshik et al. |
| 2006/0210496 A1 | 9/2006 | Mower |
| 2006/0210514 A1 | 9/2006 | Mower |
| 2006/0210515 A1 | 9/2006 | Mower |
| 2006/0210516 A1 | 9/2006 | Mower |
| 2006/0210517 A1 | 9/2006 | Mower |
| 2006/0210524 A1 | 9/2006 | Mower |
| 2006/0210609 A1 | 9/2006 | Mower |
| 2006/0210621 A1 | 9/2006 | Mower |
| 2006/0210688 A1 | 9/2006 | Mower |
| 2006/0210692 A1 | 9/2006 | Mower |
| 2006/0210697 A1 | 9/2006 | Mower |
| 2006/0211652 A1 | 9/2006 | Mower |
| 2006/0234948 A1 | 10/2006 | Empie et al. |
| 2007/0009576 A1 | 1/2007 | Stillman |
| 2007/0020358 A1 | 1/2007 | Mower |
| 2007/0026129 A1 | 2/2007 | Pandey et al. |
| 2007/0042103 A1 | 2/2007 | Cho et al. |
| 2007/0042104 A1 | 2/2007 | Cho et al. |
| 2007/0042106 A1 | 2/2007 | Wagner et al. |
| 2007/0042107 A1 | 2/2007 | Kenneth et al. |
| 2007/0082025 A1 | 4/2007 | Catani et al. |
| 2007/0082026 A1 | 4/2007 | Aimutis, Jr. et al. |
| 2007/0082028 A1 | 4/2007 | Aimutis, Jr. et al. |
| 2007/0082029 A1 | 4/2007 | Aimutis et al. |
| 2007/0082084 A1 | 4/2007 | Catani et al. |
| 2007/0082107 A1 | 4/2007 | Aimutis, Jr. et al. |
| 2007/0082108 A1 | 4/2007 | Aimutis, Jr. et al. |
| 2007/0082114 A1 | 4/2007 | Catani |
| 2007/0087036 A1 | 4/2007 | Durschlag et al. |
| 2007/0087038 A1 | 4/2007 | Richardson et al. |
| 2007/0116800 A1 | 5/2007 | Prakash et al. |
| 2007/0116819 A1 | 5/2007 | Prakash et al. |
| 2007/0116820 A1 | 5/2007 | Prakash et al. |
| 2007/0116821 A1 | 5/2007 | Prakash et al. |
| 2007/0116822 A1 | 5/2007 | Prakash et al. |
| 2007/0116823 A1 | 5/2007 | Prakash et al. |
| 2007/0116824 A1 | 5/2007 | Prakash et al. |
| 2007/0116825 A1 | 5/2007 | Prakash et al. |
| 2007/0116826 A1 | 5/2007 | Prakash et al. |
| 2007/0116827 A1 | 5/2007 | Prakash et al. |
| 2007/0116828 A1 | 5/2007 | Prakash et al. |
| 2007/0116829 A1 | 5/2007 | Prakash et al. |
| 2007/0116830 A1 | 5/2007 | Prakash et al. |
| 2007/0116831 A1 | 5/2007 | Prakash et al. |
| 2007/0116832 A1 | 5/2007 | Prakash et al. |
| 2007/0116833 A1 | 5/2007 | Prakash et al. |
| 2007/0116834 A1 | 5/2007 | Prakash et al. |
| 2007/0116835 A1 | 5/2007 | Prakash et al. |
| 2007/0116836 A1 | 5/2007 | Prakash et al. |
| 2007/0116837 A1 | 5/2007 | Prakash et al. |
| 2007/0116838 A1 | 5/2007 | Prakash et al. |
| 2007/0116839 A1 | 5/2007 | Prakash et al. |
| 2007/0116840 A1 | 5/2007 | Prakash et al. |
| 2007/0116841 A1 | 5/2007 | Prakash et al. |
| 2007/0134390 A1 | 6/2007 | Prakash et al. |
| 2007/0134391 A1 | 6/2007 | Prakash et al. |
| 2007/0148324 A1 | 6/2007 | Lin et al. |
| 2007/0149478 A1 | 6/2007 | McAnalley et al. |
| 2007/0151569 A1 | 7/2007 | Catani et al. |
| 2007/0160735 A1 | 7/2007 | Stillman |
| 2007/0178140 A1 | 8/2007 | Aimutis, Jr. et al. |
| 2007/0196539 A1 | 8/2007 | Yang et al. |
| 2007/0224321 A1 | 9/2007 | Prakash et al. |
| 2007/0275118 A1 | 11/2007 | Van Laere et al. |
| 2007/0281056 A1 | 12/2007 | Whittle et al. |
| 2008/0014327 A1 | 1/2008 | Stillman |
| 2008/0026038 A1 | 1/2008 | Steele et al. |
| 2008/0031928 A1 | 2/2008 | Steele et al. |
| 2008/0089978 A1 | 4/2008 | Grigg et al. |
| 2008/0166453 A1 | 7/2008 | Steele et al. |
| 2008/0175957 A1 | 7/2008 | Horgan et al. |
| 2009/0004220 A1 | 1/2009 | McAnalley et al. |
| 2009/0035436 A1 | 2/2009 | Leshik et al. |
| 2009/0068281 A1 | 3/2009 | Toyomura et al. |
| 2009/0074917 A2 | 3/2009 | Steele et al. |
| 2009/0143329 A1 | 6/2009 | Suzuki et al. |
| 2009/0155409 A1 | 6/2009 | Sexton et al. |
| 2009/0169682 A1 | 7/2009 | Okumura et al. |
| 2009/0181145 A1 | 7/2009 | Pandev et al. |
| 2009/0274791 A1 | 11/2009 | Mattson et al. |
| 2010/0055281 A1 | 3/2010 | Barrow et al. |
| 2010/0256090 A1 | 10/2010 | Yu et al. |
| 2010/0260904 A1 | 10/2010 | Aimutis et al. |
| 2010/0330211 A1 | 12/2010 | Mower |
| 2011/0008485 A1 | 1/2011 | Minor et al. |
| 2011/0021421 A1 | 1/2011 | Kiers et al. |
| 2011/0038982 A1 | 2/2011 | Sliwinski et al. |
| 2011/0038984 A1 | 2/2011 | Anfinsen et al. |
| 2011/0059165 A1 | 3/2011 | Gaserod et al. |
| 2011/0059166 A1 | 3/2011 | Gaserod et al. |
| 2011/0104336 A1 | 5/2011 | Stillman |
| 2011/0135568 A1 | 6/2011 | Holahan |
| 2011/0135799 A1 | 6/2011 | Holahan |
| 2011/0151094 A1 | 6/2011 | Foo et al. |
| 2011/0195101 A1 | 8/2011 | Andersen et al. |
| 2011/0200732 A1 | 8/2011 | Kielmeyer et al. |
| 2011/0257089 A1 | 10/2011 | Huisman et al. |
| 2012/0015039 A1 | 1/2012 | Sexton et al. |

FOREIGN PATENT DOCUMENTS

| | | | |
|---|---|---|---|
| AT | 347037 | B | 12/1978 |
| AT | 41288 | T | 4/1989 |
| AT | 49700 | T | 2/1990 |
| AT | 162958 | T | 2/1998 |
| AT | 188380 | T | 1/2000 |
| AT | 218065 | T | 6/2002 |
| AT | 237956 | T | 5/2003 |
| AT | 311763 | T | 12/2005 |
| AT | 355068 | T | 3/2006 |
| AT | 334688 | T | 8/2006 |
| AT | 394096 | T | 5/2008 |
| AT | 406875 | T | 9/2008 |
| AT | 421338 | T | 2/2009 |
| AT | 471084 | T | 7/2010 |
| AT | 515951 | T | 7/2011 |
| AU | 7381981 | A | 3/1982 |
| AU | 5440786 | A | 9/1987 |
| AU | 6025986 | A | 1/1988 |
| AU | 571773 | B2 | 4/1988 |
| AU | 591148 | B2 | 11/1989 |
| AU | 703527 | B2 | 3/1990 |
| AU | 7023991 | | 8/1991 |
| AU | 7415891 | A | 10/1991 |
| AU | 6750294 | A | 1/1995 |
| AU | 5719394 | A | 6/1995 |
| AU | 660812 | B2 | 7/1995 |
| AU | 1467695 | A | 8/1995 |
| AU | 5176796 | | 10/1996 |

| | | | | | | |
|---|---|---|---|---|---|---|
| AU | 675542 | B2 | 2/1997 | CA | 2046345 C | 8/1996 |
| AU | 679708 | | 7/1997 | CA | 2182061 A1 | 2/1997 |
| AU | 2355297 | | 11/1997 | CA | 2182249 | 2/1997 |
| AU | 3819997 | | 3/1998 | CA | 2205517 A1 | 11/1997 |
| AU | 5399798 | A | 7/1998 | CA | 2 262 972 A1 | 2/1998 |
| AU | 5399898 | A | 7/1998 | CA | 2276011 A1 | 7/1998 |
| AU | 3642699 | A | 11/1999 | CA | 2369946 A1 | 11/2000 |
| AU | 4543700 | | 11/2000 | CA | 2373473 A1 | 11/2000 |
| AU | 4992399 | A | 12/2000 | CA | 2399918 A1 | 8/2001 |
| AU | 734183 | B2 | 6/2001 | CA | 2422900 A1 | 5/2002 |
| AU | 735035 | B2 | 6/2001 | CA | 2437530 A1 | 9/2002 |
| AU | 3982101 | A | 9/2001 | CA | 2484528 A1 | 6/2003 |
| AU | 734183 | C | 11/2001 | CA | 2509715 A1 | 8/2004 |
| AU | 5268901 | A | 11/2001 | CA | 2509715 C | 8/2004 |
| AU | 9619601 | A | 5/2002 | CA | 2694872 A1 | 8/2004 |
| AU | 2002366638 | A1 | 6/2003 | CA | 2521531 A1 | 11/2004 |
| AU | 2003219623 | A1 | 10/2003 | CA | 2530216 A1 | 11/2004 |
| AU | 2003297428 | A1 | 7/2004 | CA | 2708045 A1 | 11/2004 |
| AU | 2003297428 | A8 | 7/2004 | CA | 2714572 A1 | 11/2004 |
| AU | 2004209974 | A1 | 8/2004 | CA | 2529491 A1 | 12/2004 |
| AU | 2003236156 | A1 | 1/2005 | CA | 2 584 188 A1 | 4/2005 |
| AU | 2003304197 | A1 | 1/2005 | CA | 2 576 344 A1 | 2/2006 |
| AU | 2004281184 | C1 | 4/2005 | CA | 2 576 344 C | 2/2006 |
| AU | 782727 | B2 | 8/2005 | CA | 2 576 375 A1 | 2/2006 |
| AU | 2005213302 | A1 | 8/2005 | CA | 2 576 375 C | 2/2006 |
| AU | 2005272802 | A1 | 2/2006 | CA | 2276011 C | 3/2006 |
| AU | 2005272802 | B2 | 2/2006 | CA | 2 499 442 A1 | 8/2006 |
| AU | 2005272922 | B2 | 2/2006 | CA | 2 601 315 A1 | 9/2006 |
| AU | 2001296196 | B2 | 7/2006 | CA | 2 604 595 A1 | 10/2006 |
| AU | 782727 | C | 9/2006 | CA | 2 606 724 A1 | 11/2006 |
| AU | 2006227390 | A1 | 9/2006 | CA | 2 552 313 A1 | 1/2007 |
| AU | 2002244694 | B2 | 10/2006 | CA | 2 552 313 C | 1/2007 |
| AU | 2006232344 | A1 | 10/2006 | CA | 2 614 348 A1 | 1/2007 |
| AU | 2006242246 | A1 | 11/2006 | CA | 2 615 646 A1 | 2/2007 |
| AU | 2006269568 | A1 | 1/2007 | CA | 2 629 983 A1 | 5/2007 |
| AU | 2006279487 | A1 | 2/2007 | CA | 2 630 042 A1 | 5/2007 |
| AU | 2006316309 | A1 | 5/2007 | CA | 2 630 043 A1 | 5/2007 |
| AU | 2006316313 | A1 | 5/2007 | CA | 2 630 048 A1 | 5/2007 |
| AU | 2006318698 | A1 | 5/2007 | CA | 2 630 051 A1 | 5/2007 |
| AU | 2006318700 | A1 | 5/2007 | CA | 2 630 052 A1 | 5/2007 |
| AU | 2006318708 | A1 | 5/2007 | CA | 2 630 054 A1 | 5/2007 |
| AU | 2006318711 | A1 | 5/2007 | CA | 2 630 055 A1 | 5/2007 |
| AU | 2006318712 | A1 | 5/2007 | CA | 2 630 056 A1 | 5/2007 |
| AU | 2006318751 | A1 | 5/2007 | CA | 2 630 059 A1 | 5/2007 |
| AU | 2006318752 | A1 | 5/2007 | CA | 2 630 060 A1 | 5/2007 |
| AU | 2006318753 | A1 | 5/2007 | CA | 2 630 080 A1 | 5/2007 |
| AU | 2006318764 | A1 | 5/2007 | CA | 2 630 131 A1 | 5/2007 |
| AU | 2006318765 | A1 | 5/2007 | CA | 2 630 141 A1 | 5/2007 |
| AU | 2006318766 | A1 | 5/2007 | CA | 2 630 142 A1 | 5/2007 |
| AU | 2006318783 | A1 | 5/2007 | CA | 2 630 143 A1 | 5/2007 |
| AU | 2006318788 | A1 | 5/2007 | CA | 2 630 144 A1 | 5/2007 |
| AU | 2006318790 | A1 | 5/2007 | CA | 2 630 145 A1 | 5/2007 |
| AU | 2006318795 | A1 | 5/2007 | CA | 2 629 974 A1 | 6/2007 |
| AU | 2006318796 | A1 | 5/2007 | CA | 2 630 208 A1 | 10/2007 |
| AU | 2006325130 | A1 | 6/2007 | CA | 2 643 662 A1 | 10/2007 |
| AU | 2004209974 | B2 | 7/2007 | CA | 2 630 031 A1 | 12/2007 |
| AU | 2007217851 | A1 | 8/2007 | CA | 2373473 C | 2/2008 |
| AU | 2006341542 | A1 | 10/2007 | CA | 2 262 972 C | 7/2008 |
| AU | 2007238985 | A1 | 10/2007 | CA | 2 674 422 A1 | 7/2008 |
| AU | 2006344337 | A1 | 12/2007 | CA | 2733901 | 3/2010 |
| AU | 2001239821 | C1 | 3/2008 | CA | 2 740 910 A1 | 4/2010 |
| AU | 2007317460 | A1 | 5/2008 | CA | 2509715 C | 5/2010 |
| AU | 2008206670 | A1 | 7/2008 | CA | 2 747 659 A1 | 7/2010 |
| AU | 2008361201 | A1 | 3/2010 | CA | 2530216 C | 8/2010 |
| AU | 2009304323 | A1 | 4/2010 | CA | 2 756 765 | 10/2010 |
| AU | 2004281184 | B2 | 6/2011 | CA | 2529491 C | 10/2011 |
| AU | 2009335743 | A1 | 8/2011 | CH | 610731 A5 | 5/1979 |
| AU | 2010233000 | A1 | 10/2011 | CN | 86101752 A | 10/1986 |
| BE | 826675 | A1 | 9/1975 | CN | 1010584 B | 11/1990 |
| CA | 1041013 | A1 | 10/1978 | CN | 1104890 A | 7/1995 |
| CA | 1263404 | A1 | 11/1989 | CN | 1122101 | 6/1996 |
| CA | 2166735 | C | 7/1990 | CN | 1126091 * | 7/1996 |
| CA | 2035529 | A1 | 10/1991 | CN | 1126091 | 7/1996 |
| CA | 2035529 | C | 10/1991 | CN | 1179705 | 4/1998 |
| CA | 2039947 | | 10/1991 | CN | 1227495 A | 9/1999 |
| CA | 2128160 | A1 | 1/1995 | CN | 1241912 A | 1/2000 |
| CA | 2177466 | A1 | 6/1995 | CN | 1061514 C | 2/2001 |
| CA | 2166735 | | 7/1996 | CN | 1284297 A | 2/2001 |
| CA | 2046345 | A1 | 8/1996 | CN | 1299238 A | 6/2001 |

| | | | | | | |
|---|---|---|---|---|---|---|
| CN | 1086277 | C | 6/2002 | EP | 0 046 639 A1 | 3/1982 |
| CN | 1404364 | A | 3/2003 | EP | 0 195 730 A2 | 9/1986 |
| CN | 1115966 | C | 7/2003 | EP | 0 195 731 A2 | 9/1986 |
| CN | 1431870 | A | 7/2003 | EP | 0 195 731 A3 | 9/1986 |
| CN | 1457704 | A | 11/2003 | EP | 0 195 731 B1 | 9/1986 |
| CN | 1211019 | C | 7/2005 | EP | 0 195 730 A3 | 7/1987 |
| CN | 1655769 | A | 8/2005 | EP | 0441495 A2 | 8/1991 |
| CN | 1221188 | C | 10/2005 | EP | 0 452 262 A2 | 10/1991 |
| CN | 1695488 | A | 11/2005 | EP | 0 457 919 A1 | 11/1991 |
| CN | 1777415 | A | 5/2006 | EP | 0 457 919 A4 | 11/1991 |
| CN | 1787750 | A | 6/2006 | EP | 0 452 262 A3 | 4/1992 |
| CN | 1262213 | C | 7/2006 | EP | 0441495 A3 | 9/1992 |
| CN | 1819815 | A | 8/2006 | EP | 0 648 495 A2 | 4/1995 |
| CN | 1852659 | A | 10/2006 | EP | 0 648 495 A3 | 8/1995 |
| CN | 1879507 | A | 12/2006 | EP | 0 452 262 B1 | 1/1996 |
| CN | 101001536 | A | 7/2007 | EP | 0 730 494 A1 | 9/1996 |
| CN | 101001537 | A | 7/2007 | EP | 0 743 011 A1 | 11/1996 |
| CN | 101011082 | A | 8/2007 | EP | 0 757 895 A2 | 2/1997 |
| CN | 101166544 | A | 4/2008 | EP | 0 758 831 A2 | 2/1997 |
| CN | 101171037 | A | 4/2008 | EP | 0 757 895 A3 | 7/1997 |
| CN | 101188948 | A | 5/2008 | EP | 0 758 531 A3 | 7/1997 |
| CN | 101242744 | A | 8/2008 | EP | 0 808 580 A2 | 11/1997 |
| CN | 101287382 | A | 10/2008 | EP | 0 808 580 A3 | 11/1997 |
| CN | 101291589 | A | 10/2008 | EP | 0 730 494 B1 | 2/1998 |
| CN | 101306011 | A | 11/2008 | EP | 0743011 A4 | 10/1998 |
| CN | 101309598 | A | 11/2008 | EP | 0 923 382 A1 | 6/1999 |
| CN | 101309599 | A | 11/2008 | EP | 0 923 382 A4 | 6/1999 |
| CN | 101309600 | A | 11/2008 | EP | 0 948 265 A1 | 10/1999 |
| CN | 101309601 | A | 11/2008 | EP | 0 648 495 B1 | 1/2000 |
| CN | 101309602 | A | 11/2008 | EP | 1 075 188 A1 | 2/2001 |
| CN | 101312653 | A | 11/2008 | EP | 1 075 188 A4 | 2/2001 |
| CN | 101312658 | A | 11/2008 | EP | 1 172 041 A2 | 1/2002 |
| CN | 101312659 | A | 11/2008 | EP | 1 172 041 A3 | 1/2002 |
| CN | 101312660 | A | 11/2008 | EP | 1 172 041 B1 | 1/2002 |
| CN | 101312662 | A | 11/2008 | EP | 1 172 041 B2 | 1/2002 |
| CN | 101312663 | A | 11/2008 | EP | 1 172 041 B9 | 1/2002 |
| CN | 101330833 | A | 12/2008 | EP | 1 173 066 A1 | 1/2002 |
| CN | 101340821 | A | 1/2009 | EP | 1 178 811 A1 | 2/2002 |
| CN | 101340824 | A | 1/2009 | EP | 0 948 265 B1 | 4/2002 |
| CN | 101340826 | A | 1/2009 | EP | 0 923 382 B1 | 5/2002 |
| CN | 101340827 | A | 1/2009 | EP | 1 228 769 A1 | 8/2002 |
| CN | 101346074 | A | 1/2009 | EP | 1 259 128 A1 | 11/2002 |
| CN | 101365347 | A | 2/2009 | EP | 1 281 323 A1 | 2/2003 |
| CN | 101365348 | A | 2/2009 | EP | 1 281 323 A4 | 2/2003 |
| CN | 101378667 | A | 3/2009 | EP | 1 328 280 A1 | 7/2003 |
| CN | 101394756 | A | 3/2009 | EP | 1 390 071 A2 | 2/2004 |
| CN | 101472485 | A | 7/2009 | EP | 0 743 011 B1 | 3/2004 |
| CN | 101500435 | A | 8/2009 | EP | 1 259 128 A4 | 3/2004 |
| CN | 101553133 | A | 10/2009 | EP | 1 463 515 A2 | 10/2004 |
| CN | 101631476 | A | 1/2010 | EP | 1 463 515 A4 | 1/2005 |
| CN | 101632434 | A | 1/2010 | EP | 1 496 871 A1 | 1/2005 |
| CN | 101632435 | A | 1/2010 | EP | 1 075 188 B1 | 11/2005 |
| CN | 1655769 | B | 5/2010 | EP | 1 590 004 A1 | 11/2005 |
| CN | 101731623 | A | 6/2010 | EP | 1 633 211 A1 | 3/2006 |
| CN | 101889027 | A | 11/2010 | EP | 1 681 937 A1 | 7/2006 |
| CN | 1787750 | B | 12/2010 | EP | 1 328 280 B1 | 8/2006 |
| CN | 101909468 | A | 12/2010 | EP | 1 694 312 A1 | 8/2006 |
| CN | 101919827 | A | 12/2010 | EP | 1 732 401 A2 | 12/2006 |
| CN | 101925307 | A | 12/2010 | EP | 1 178 811 B1 | 2/2007 |
| CN | 101938911 | A | 1/2011 | EP | 1 786 272 A1 | 5/2007 |
| CN | 1852659 | B | 2/2011 | EP | 1 791 433 A2 | 6/2007 |
| CN | 1695488 | B | 3/2011 | EP | 1 806 971 A1 | 7/2007 |
| CN | 102077854 | A | 6/2011 | EP | 1 858 555 A2 | 11/2007 |
| CN | 102077939 | A | 6/2011 | EP | 1 876 914 A2 | 1/2008 |
| CN | 102077940 | A | 6/2011 | EP | 1 877 094 A1 | 1/2008 |
| CN | 102077944 | A | 6/2011 | EP | 1 906 759 A2 | 4/2008 |
| CN | 102131395 | A | 7/2011 | EP | 1 694 312 B1 | 5/2008 |
| CN | 1777415 | B | 11/2011 | EP | 1 924 153 A2 | 5/2008 |
| CN | 101306011 | B | 11/2011 | EP | 1 924 157 A2 | 5/2008 |
| CN | 102264246 | A | 11/2011 | EP | 1 931 222 A2 | 6/2008 |
| CN | 102308994 | A | 1/2012 | EP | 1 959 744 A1 | 8/2008 |
| CN | 102316752 | A | 1/2012 | EP | 1 959 754 A1 | 8/2008 |
| DE | 2472827 | A1 | 9/1975 | EP | 1 959 755 A1 | 8/2008 |
| DE | 2527632 | A1 | 1/1976 | EP | 1 959 756 A2 | 8/2008 |
| DE | 10 2010 038 644 | A1 | 7/2011 | EP | 1 959 757 A2 | 8/2008 |
| DK | 61775 | A | 9/1975 | EP | 1 959 758 A2 | 8/2008 |
| DK | 123486 | A | 9/1986 | EP | 1 959 759 A2 | 8/2008 |
| EE | 9900266 | A | 2/2000 | EP | 1 959 760 A1 | 8/2008 |
| EE | 03659 | B1 | 4/2002 | EP | 1 959 761 A1 | 8/2008 |

| | | | | | | |
|---|---|---|---|---|---|---|
| EP | 1 959 762 A2 | 8/2008 | | JP | 63112964 A | 5/1988 |
| EP | 1 959 763 A1 | 8/2008 | | JP | 11196761 A | 7/1990 |
| EP | 1 496 871 B1 | 9/2008 | | JP | 3-183457 | 8/1991 |
| EP | 1 962 616 A2 | 9/2008 | | JP | 3-290170 | 12/1991 |
| EP | 1 965 668 A2 | 9/2008 | | JP | 4228030 A | 8/1992 |
| EP | 1 968 399 A1 | 9/2008 | | JP | 5-186356 | 7/1993 |
| EP | 1 968 400 A1 | 9/2008 | | JP | 6237783 A | 8/1994 |
| EP | 1 971 221 A1 | 9/2008 | | JP | 7067577 A | 3/1995 |
| EP | 1 971 223 A2 | 9/2008 | | JP | 7-90002 A | 4/1995 |
| EP | 1 971 224 A1 | 9/2008 | | JP | 9103264 A | 4/1997 |
| EP | 1 971 225 A1 | 9/2008 | | JP | 9103265 A | 4/1997 |
| EP | 1 971 226 A2 | 9/2008 | | JP | 2643669 | 5/1997 |
| EP | 1 971 227 A2 | 9/2008 | | JP | H 09506342 A | 6/1997 |
| EP | 1 971 232 A1 | 9/2008 | | JP | 10042803 A | 2/1998 |
| EP | 1 971 315 A2 | 9/2008 | | JP | 2882895 B2 | 4/1999 |
| EP | 1 973 419 A2 | 10/2008 | | JP | 2939491 B2 | 8/1999 |
| EP | 1 981 349 A2 | 10/2008 | | JP | 3043070 B2 | 5/2000 |
| EP | 1 981 484 A2 | 10/2008 | | JP | 2001-509013 | 7/2001 |
| EP | 1 990 045 A1 | 11/2008 | | JP | 2002037744 A * | 2/2002 |
| EP | 1 993 386 A2 | 11/2008 | | JP | 2002-511051 | 4/2002 |
| EP | 2 007 224 A2 | 12/2008 | | JP | 2002-512929 | 5/2002 |
| EP | 1 590 004 B1 | 1/2009 | | JP | 2003-500361 | 1/2003 |
| EP | 2 065 046 A1 | 6/2009 | | JP | 2003-534777 | 11/2003 |
| EP | 2 070 551 A1 | 6/2009 | | JP | 2004-512306 | 4/2004 |
| EP | 2 091 355 A2 | 8/2009 | | JP | 2005-29513 | 2/2005 |
| EP | 2 124 608 A2 | 12/2009 | | JP | 2005-503332 | 2/2005 |
| EP | 1 993 386 A4 | 5/2010 | | JP | 2005-526819 | 9/2005 |
| EP | 1 633 211 B1 | 6/2010 | | JP | 2005-348731 | 12/2005 |
| EP | 2 230 940 A1 | 9/2010 | | JP | 2006-516995 | 7/2006 |
| EP | 2 230 941 A1 | 9/2010 | | JP | 2006-524193 | 10/2006 |
| EP | 2 249 666 A1 | 11/2010 | | JP | 2006-342085 | 12/2006 |
| EP | 2 328 418 A1 | 6/2011 | | JP | 2006-527700 | 12/2006 |
| EP | 2 337 458 A1 | 6/2011 | | JP | 2007-508822 | 4/2007 |
| EP | 1 281 323 B1 | 7/2011 | | JP | 2007-131620 | 5/2007 |
| EP | 2 346 356 A1 | 7/2011 | | JP | 2007-520232 | 7/2007 |
| EP | 2 389 075 A1 | 11/2011 | | JP | 2007-246541 | 9/2007 |
| EP | 1 681 937 A4 | 1/2012 | | JP | 4059908 B2 | 12/2007 |
| EP | 2 413 713 A1 | 2/2012 | | JP | 2008-509665 | 4/2008 |
| ES | 8702882 A1 | 4/1987 | | JP | 2008-509922 | 4/2008 |
| ES | 8707491 A1 | 10/1987 | | JP | 2008-183013 | 8/2008 |
| ES | 2369102 A1 | 11/2011 | | JP | 2008-532555 | 8/2008 |
| FI | 910534 A | 8/1991 | | JP | 2008-537678 | 9/2008 |
| FI | 911683 A | 10/1991 | | JP | 2008-539729 | 11/2008 |
| FI | 943296 A | 1/1995 | | JP | 2009-500034 | 1/2009 |
| FI | 962203 A | 7/1996 | | JP | 2009-504188 | 2/2009 |
| FI | 965251 A | 7/1998 | | JP | 2009-504765 | 2/2009 |
| FI | 20090217 A | 5/2009 | | JP | 2009-517020 | 4/2009 |
| FI | 120290 B1 | 9/2009 | | JP | 2009-517021 | 4/2009 |
| FR | 2 263 704 A1 | 10/1975 | | JP | 2009-517023 | 4/2009 |
| FR | 2 275 153 A1 | 1/1976 | | JP | 2009-517024 | 4/2009 |
| FR | 2 275 153 B1 | 10/1978 | | JP | 2009-517025 | 4/2009 |
| FR | 2 263 704 B1 | 12/1978 | | JP | 2009-517026 | 4/2009 |
| FR | 2 579 201 A1 | 9/1986 | | JP | 2009-517027 | 4/2009 |
| FR | 2 579 202 A1 | 9/1986 | | JP | 2009-517028 | 4/2009 |
| FR | 2 579 201 B1 | 5/1987 | | JP | 2009-517029 | 4/2009 |
| FR | 2 597 096 A1 | 10/1987 | | JP | 2009-517030 | 4/2009 |
| FR | 2 579 202 B1 | 4/1988 | | JP | 2009-517031 | 4/2009 |
| FR | 2 606 404 A2 | 5/1988 | | JP | 2009-517032 | 4/2009 |
| FR | 2 597 096 B1 | 6/1988 | | JP | 2009-517033 | 4/2009 |
| FR | 2 606 404 B2 | 11/1991 | | JP | 2009-517034 | 4/2009 |
| FR | 2 690 445 A1 | 10/1993 | | JP | 2009-517035 | 4/2009 |
| FR | 2 690 445 B1 | 11/1994 | | JP | 2009-517036 | 4/2009 |
| GB | 1 471 398 A | 4/1977 | | JP | 2009-517038 | 4/2009 |
| GB | 1 480 967 A | 7/1977 | | JP | 2009-517039 | 4/2009 |
| GB | 2 416 981 A | 2/2006 | | JP | 2009-517040 | 4/2009 |
| GB | 2 418 856 A | 4/2006 | | JP | 2009-517041 | 4/2009 |
| GB | 2 418 856 A8 | 4/2006 | | JP | 2009-517042 | 4/2009 |
| GB | 2 418 856 B | 8/2007 | | JP | 2009-517043 | 4/2009 |
| GB | 2 418 856 B8 | 8/2007 | | JP | 2009-517044 | 4/2009 |
| GB | 2474937 A | 5/2011 | | JP | 2009-517384 | 4/2009 |
| GB | 2474938 A | 5/2011 | | JP | 2009-517385 | 4/2009 |
| GB | 2474939 A | 5/2011 | | JP | 2009-523407 | 6/2009 |
| GB | 2474940 A | 5/2011 | | JP | 2009-149621 | 7/2009 |
| GB | 2474941 A | 5/2011 | | JP | 2009-524575 | 7/2009 |
| GR | 860583 A1 | 7/1986 | | JP | 2009-527252 | 7/2009 |
| IE | 910368 A1 | 8/1991 | | JP | 4302318 B2 | 7/2009 |
| JP | 51017315 A | 2/1976 | | JP | 2009-533490 | 9/2009 |
| JP | 61219352 A | 9/1986 | | JP | 2010-508823 | 3/2010 |
| JP | 61219353 A | 9/1986 | | JP | 2010-516246 | 5/2010 |

| | | | | | | |
|---|---|---|---|---|---|---|
| JP | 2010-285447 | 12/2010 | | WO | WO 02/067986 A3 | 9/2006 |
| JP | 4607261 B2 | 1/2011 | | WO | WO 2006/102108 A2 | 9/2006 |
| JP | 4615812 B2 | 1/2011 | | WO | WO 2006/102108 A3 | 9/2006 |
| JP | 2011-67220 | 4/2011 | | WO | WO 2006/103750 A1 | 10/2006 |
| JP | 2011-87597 | 5/2011 | | WO | WO 2006/107820 A2 | 10/2006 |
| JP | 2011-98982 | 5/2011 | | WO | WO 2006/107820 A3 | 10/2006 |
| JP | 2011-115177 | 6/2011 | | WO | WO 2006/119286 A1 | 11/2006 |
| JP | 2011-135889 | 7/2011 | | WO | WO 2007/008384 A2 | 1/2007 |
| JP | 4717311 B2 | 7/2011 | | WO | WO 2007/008384 A3 | 1/2007 |
| JP | 4741625 B2 | 8/2011 | | WO | WO 2007/022312 A2 | 2/2007 |
| JP | 4790220 B2 | 10/2011 | | WO | WO 2007/022312 A3 | 2/2007 |
| JP | 2011-254834 | 12/2011 | | WO | WO 2007/022313 A2 | 2/2007 |
| JP | 2012-16356 | 1/2012 | | WO | WO 2007/022313 A3 | 2/2007 |
| KR | 930004456 B1 | 5/1993 | | WO | WO 2007/022341 A2 | 2/2007 |
| KR | 0157425 B1 | 10/1998 | | WO | WO 2007/022341 A3 | 2/2007 |
| KR | 2000-0029878 | 5/2000 | | WO | WO 2007/039294 A2 | 4/2007 |
| KR | 2000-0069761 | 11/2000 | | WO | WO 2007/039294 A3 | 4/2007 |
| KR | 2002-0011991 | 2/2002 | | WO | WO 2007/043656 A1 | 4/2007 |
| KR | 2002-0086556 | 11/2002 | | WO | WO 2007/044547 A1 | 4/2007 |
| KR | 10-2003-0003272 | 1/2003 | | WO | WO 2007/044580 A1 | 4/2007 |
| KR | 10-2004-0040890 | 5/2004 | | WO | WO 2007/044611 A2 | 4/2007 |
| KR | 10-0450097 B1 | 9/2004 | | WO | WO 2007/044611 A3 | 4/2007 |
| KR | 10-2005-0025151 A | 3/2005 | | WO | WO 2007/044637 A1 | 4/2007 |
| KR | 10-0541324 B1 | 1/2006 | | WO | WO 2007/044638 A1 | 4/2007 |
| KR | 10-0689118 B1 | 3/2007 | | WO | WO 2007/044663 A1 | 4/2007 |
| KR | 10-0729478 B1 | 6/2007 | | WO | WO 2007/044665 A2 | 4/2007 |
| KR | 10-2008-0003796 | 1/2008 | | WO | WO 2007/044665 A3 | 4/2007 |
| KR | 10-2008-0007449 | 1/2008 | | WO | WO 2007/044723 A2 | 4/2007 |
| KR | 10-2008-0055788 | 6/2008 | | WO | WO 2007/044723 A3 | 4/2007 |
| KR | 10-2008-0067384 A | 7/2008 | | WO | WO 2007/044737 A2 | 4/2007 |
| KR | 10-2008-009616 | 11/2008 | | WO | WO 2007/044737 A3 | 4/2007 |
| KR | 10-2009-0029699 A | 3/2009 | | WO | WO 2007/061753 A2 | 5/2007 |
| KR | 10-2010-0123780 A | 11/2010 | | WO | WO 2007/061753 A3 | 5/2007 |
| NL | 7501972 A | 9/1975 | | WO | WO 2007/061757 A1 | 5/2007 |
| NL | 7507403 A | 12/1975 | | WO | WO 2007/061794 A2 | 5/2007 |
| PT | 82216 A | 4/1986 | | WO | WO 2007/061794 A3 | 5/2007 |
| PT | 82216 B | 8/1987 | | WO | WO 2007/061796 A2 | 5/2007 |
| PT | 96660 A | 10/1991 | | WO | WO 2007/061796 A3 | 5/2007 |
| PT | 948265 E | 8/2003 | | WO | WO 2007/061797 A2 | 5/2007 |
| RU | 2009109859 A | 9/2010 | | WO | WO 2007/061797 A3 | 5/2007 |
| RU | 2 403 809 C1 | 11/2010 | | WO | WO 2007/061802 A1 | 5/2007 |
| SE | 7501886 A | 9/1975 | | WO | WO 2007/061803 A1 | 5/2007 |
| SE | 404289 B | 10/1978 | | WO | WO 2007/061804 A2 | 5/2007 |
| SE | 404289 C | 1/1979 | | WO | WO 2007/061804 A3 | 5/2007 |
| WO | WO 91/08679 A1 | 6/1991 | | WO | WO 2007/061809 A2 | 5/2007 |
| WO | WO 95/14531 A1 | 6/1995 | | WO | WO 2007/061809 A3 | 5/2007 |
| WO | WO 95/20323 A1 | 8/1995 | | WO | WO 2007/061810 A2 | 5/2007 |
| WO | WO 96/29889 A1 | 10/1996 | | WO | WO 2007/061810 A3 | 5/2007 |
| WO | WO 98/06418 A1 | 2/1998 | | WO | WO 2007/061858 A1 | 5/2007 |
| WO | WO 98/28989 A1 | 7/1998 | | WO | WO 2007/061859 A1 | 5/2007 |
| WO | WO 98/28990 A1 | 7/1998 | | WO | WO 2007/061860 A1 | 5/2007 |
| WO | WO 99/56556 A1 | 11/1999 | | WO | WO 2007/061860 A8 | 5/2007 |
| WO | WO 00/64268 A1 | 11/2000 | | WO | WO 2007/061861 A2 | 5/2007 |
| WO | WO 00/71137 A1 | 11/2000 | | WO | WO 2007/061861 A3 | 5/2007 |
| WO | WO 01/62108 A1 | 8/2001 | | WO | WO 2007/061871 A1 | 5/2007 |
| WO | WO 01/84948 A1 | 11/2001 | | WO | WO 2007/061872 A2 | 5/2007 |
| WO | WO 02/34271 A1 | 5/2002 | | WO | WO 2007/061872 A3 | 5/2007 |
| WO | WO 02/078463 A1 | 10/2002 | | WO | WO 2007/061873 A1 | 5/2007 |
| WO | WO 03/049689 A2 | 6/2003 | | WO | WO 2007/061898 A1 | 5/2007 |
| WO | WO 03/049689 A3 | 6/2003 | | WO | WO 2007/061900 A1 | 5/2007 |
| WO | WO 03/084516 A1 | 10/2003 | | WO | WO 2007/061907 A2 | 5/2007 |
| WO | WO 2004/057985 A2 | 7/2004 | | WO | WO 2007/061907 A3 | 5/2007 |
| WO | WO 2004/057985 A3 | 7/2004 | | WO | WO 2007/061908 A1 | 5/2007 |
| WO | WO 2004/069179 A2 | 8/2004 | | WO | WO 2007/061911 A2 | 5/2007 |
| WO | WO 2004/069179 A3 | 8/2004 | | WO | WO 2007/061911 A3 | 5/2007 |
| WO | WO 2004/093862 A1 | 11/2004 | | WO | WO 2007/061912 A2 | 5/2007 |
| WO | WO 2004/093863 A1 | 11/2004 | | WO | WO 2007/061912 A3 | 5/2007 |
| WO | WO 2004/110178 A1 | 12/2004 | | WO | WO 2007/070224 A2 | 6/2007 |
| WO | WO 2004/112773 A1 | 12/2004 | | WO | WO 2007/070224 A3 | 6/2007 |
| WO | WO 2005/002536 A1 | 1/2005 | | WO | WO 2007/098092 A2 | 8/2007 |
| WO | WO 2005/036971 A1 | 4/2005 | | WO | WO 2007/098092 A3 | 8/2007 |
| WO | WO 2005/048995 A1 | 6/2005 | | WO | WO 2007/117281 A2 | 10/2007 |
| WO | WO 2005/076821 A2 | 8/2005 | | WO | WO 2007/117281 A3 | 10/2007 |
| WO | WO 2005/076821 A3 | 8/2005 | | WO | WO 2007/120500 A2 | 10/2007 |
| WO | WO 2006/016170 A2 | 2/2006 | | WO | WO 2007/120500 A3 | 10/2007 |
| WO | WO 2006/016170 A3 | 2/2006 | | WO | WO 2007/142680 A1 | 12/2007 |
| WO | WO 2006/020686 A1 | 2/2006 | | WO | WO 2008/056967 A1 | 5/2008 |
| WO | WO 2006/020754 A1 | 2/2006 | | WO | WO 2008/057965 A2 | 5/2008 |
| WO | WO 02/067986 A2 | 9/2006 | | WO | WO 2008/057965 A3 | 5/2008 |

| | | | |
|---|---|---|---|
| WO | WO 2008/087607 A2 | 7/2008 |
| WO | WO 2008/087607 A3 | 7/2008 |
| WO | WO 2009/072884 A1 | 6/2009 |
| WO | WO 2009/072885 A1 | 6/2009 |
| WO | WO 2009/072886 A1 | 6/2009 |
| WO | WO 2009/079537 A1 | 6/2009 |
| WO | WO 2009/086685 A1 | 7/2009 |
| WO | WO 2010/022764 A1 | 3/2010 |
| WO | WO 2010/043332 A1 | 4/2010 |
| WO | WO 2010/047581 A1 | 4/2010 |
| WO | WO 2010/047597 A1 | 4/2010 |
| WO | WO 2010/080557 A1 | 7/2010 |
| WO | WO 2010/114627 A1 | 10/2010 |
| WO | WO 2011/024199 A1 | 3/2011 |
| WO | WO 2011/024199 A4 | 3/2011 |
| WO | WO 2011/031617 A2 | 3/2011 |
| WO | WO 2011/031617 A3 | 3/2011 |
| WO | WO 2011/031621 A2 | 3/2011 |
| WO | WO 2011/031621 A3 | 3/2011 |
| WO | WO 2011/051650 A1 | 5/2011 |
| WO | WO 2011/051651 A1 | 5/2011 |
| WO | WO 2011/051652 A1 | 5/2011 |
| WO | WO 2011/051653 A1 | 5/2011 |
| WO | WO 2011/051654 A1 | 5/2011 |
| WO | WO 2011/113984 A1 | 9/2011 |

OTHER PUBLICATIONS

D. Molnár, et al., "The effect of unprocessed wheat bran on blood glucose and plasma immunoreactive insulin levels during oral glucose tolerance test in obese children", Acta Paediatrica Hungarica, 26, (1), 1985, pp. 75-77.

S. Wakabayashi, et al., "Effects of indigestible dextrin on glucose tolerance in rats", Journal of Endocrinology 144, 1995, pp. 533-538.

Yoshiyuki Kimura, et al., "Effects of soluble sodium alginate on cholesterol excretion and glucose tolerance in rats", Journal of Ethnopharmacology 54, Elsevier, 1996, pp. 47-54.

Keisuke Tsuji, et al., "Effects of Na-Binding Capacity of Dietary Fibers on Blood Pressure in Spontaneously Hypertensive Rats", Journal of Home Economics of Japan, vol. 39, No. 3, 1988, pp. 187-195.

Wu Zhonggao, et al., "A Experimental Studies on the Hypoglycemic Effects of Haizaojing", Chinese Journal of Marine Drugs, 2000, pp. 35-36.

Hezaojing of Acadian Seaplants Limited: Improves Root Nudulation and Increases Biomass in Alfalfa, Ext. Gen. 22.11.C.0907, (2007) (with verified English translation).

Elizabeth Percival, "The Polysacharrides of Green, Red and Brown Seaweeds: Their Basic Structure, Biosynthesis and Function," *Br. Phycol. J.*, 14: 103-117 (Jun. 1, 1979).

Victor A. Gault, et al., "Chemical Ablation of Gastric Inhibitory Polypeptide Receptor Action by Daily (Pro3) GIP Administration Improves Glucose Tolerance and Ameliorates Insulin Resistance and Abnormalities of Islet Structure in Obesity-Related Diabetes," *Diabetes*, vol. 54, Aug. 2005 (2436-2005).

* cited by examiner

AGENT FOR PREVENTING OR AMELIORATING OBESITY

FIELD OF THE INVENTION

The present invention relates to an agent for preventing or ameliorating obesity, to an agent for inhibiting accumulation of visceral fat, to an agent for inhibiting accumulation of liver lipid, and to an agent for preventing or ameliorating fatty liver.

BACKGROUND OF THE INVENTION

In recent years, Japanese have consumed more of a Western diet, resulting in taking in excessive energy (increase in ingestion of fat and sucrose), and have had fewer chances for physical exercise. Therefore, the number of patients of lifestyle-related diseases such as obesity and diabetes continuously has increased. Under such social circumstances, prevention and amelioration of obesity is a key issue.

One of the methods for the preventing or ameliorating of obesity, that dieticians generally propose is to consume low-calorie or low-fat food. In recent years, it was reported that each of water-insoluble dietary fibers such as wheat bran, water-soluble dietary fibers such as indigestible dextrin, and resistant starches such as high amylose starch has an action of promoting lipid excretion (Non-Patent Document 1), an inhibitory action of sugar absorption (Non-Patent Document 2), and an action of reducing blood neutral fat (Non-Patent Document 3), respectively and these materials have an action of ameliorating glucose tolerance (Non-Patent Documents 3, 4 and 5). Thus, these materials are thought to be effective for the preventing or ameliorating of obesity.

Since a rapid rise in postprandial blood lipid level is thought to promote accumulation of fat, an approach of suppressing postprandial hyperlipidemia (increase in blood triglyceride level) is also a key issue for the prevention or amelioration of obesity. In recent years, there have been reported some safe and effective lipid-absorption inhibitors such as xanthan gum and propylene glycol alginate ester (Patent Document 1), chitosan (Patent Document 2) and a composition for ameliorating obesity containing an extract from animal meat and/or fish meat and a substance capable of suppressing fat accumulation, in combination (Patent Document 3).

It is also reported that sodium alginate, which is a high-molecular acidic polysaccharide found in brown algae, has an inhibitory action on increase in blood glucose level and thus is useful for the prevention of obesity and diabetes (Patent Document 4 and Non-Patent Document 7).

The aforementioned low-calorie food or low-fat food can exhibit a temporary effect of reducing body weight. However, since a food composing of the low-calorie food or low-fat food is generally not tasty (i.e., monotonous), such food becomes unacceptable by those who consume it over a long period, making long-term ingestion thereof difficult. Also, in order to attain the aforementioned physiological effect, the aforementioned conventional food materials such as water-insoluble dietary fiber, water-soluble dietary fiber, and resistant starch must be continuously ingested in a large amount over a long period of time. Although the physiological effect can be attained, suppression of obesity has not yet been confirmed. When foods and beverages are produced by using such food materials, their intrinsic appearance, taste, sensations such as touch to the teeth and smoothness are generally impaired. Therefore, the food materials cannot be easily incorporated into foods and beverages in a satisfactory amount, and a limitation is imposed on the type of the foods and beverages into which the food materials are added. In addition, difficulty is encountered in long-term ingestion of such foods and beverages.

Due to insolubility, making beverages containing water-insoluble dietary fiber is difficult. Resistant starch or water-soluble dietary fiber can be dissolved or dispersed in water. However, difficulty is also encountered in producing beverages containing resistant starch or water-soluble dietary fiber in a sufficient amount to expect anti-obesity effect, since the viscosity of the beverages increases.

Meanwhile, potassium alginate is widely used as a thickener for food and as a gelling agent incorporated into a dental impression material, and it is reported that a hypertension inhibitory action of potassium alginate based on active excretion of sodium in the body (Non-Patent Document 8).

However, potassium alginate has never been known to have an action of preventing or ameliorating obesity.

Patent Document

Patent Document 1: JP-A-H05-186356
Patent Document 2: JP-A-H03-290170
Patent Document 3: WO 2006/103750 Pamphlet
Patent Document 4: Japanese Patent No. 2643669

Non-Patent Document

Non-Patent Document 1: Am. J. Clin. Nutr., 1978, 31(10 Suppl): S21-S29
Non-Patent Document 2: Folia Endocrinologica Japonica, 1992, 68(6): 623-35
Non-Patent Document 3: Am. J. Clin. Nutr., 1989, 49(2): 337-44
Non-Patent Document 4: Acta Paediatr Hung., 1985, 26(1): 75-7
Non-Patent Document 5: J. Endcrinol., 1995, 144(3): 533-8
Non-Patent Document 6: Y. Kimura et al., Journal of Ethnopharmacology, 54, (1996) 47-54
Non-Patent Document 7: Keisuke Tsuji et al, Journal of Home Economics of Japan, Vol. 39, No. 3, pages 187-195 (1988)

SUMMARY OF THE INVENTION

The present invention is directed to a method for preventing or ameliorating obesity, a method for inhibiting accumulation of visceral fat, a method for inhibiting accumulation of liver lipid, and a method for preventing or ameliorating fatty liver, which methods include administering potassium alginate to a subject in need thereof or having the subject take potassium alginate.

The present invention is also directed to a method for treating or remedying obesity or for reducing the likelihood of developing obesity and a method for treating or remedying fatty liver and reducing the likelihood of developing fatty liver.

DETAILED DESCRIPTION OF THE INVENTION

The present invention provides a method for preventing or ameliorating obesity, a method for inhibiting accumulation of visceral fat, a method for inhibiting accumulation of liver lipid, and a method for preventing or ameliorating fatty liver, including using a material for a pharmaceutical product or a food, which has an inhibitory action on body weight increase, accumulation of visceral fat and/or accumulation of liver lipid.

The present inventors have investigated a material which is applied to the above product or food and is also effective in a beverage. As a result, they have found that potassium alginate has an inhibitory action on body weight increase, accumulation of visceral fat, and/or accumulation of liver lipid and exhibits the effect of preventing or ameliorating obesity or fatty liver, in the case where potassium alginate is ingested as aqueous solution or as an ingredient incorporated into a meal.

According to the present invention, in fields of pharmaceutical and food, a variety of lifestyle-related diseases such as obesity and fatty liver can be prevented, treated, or ameliorated.

Alginic acid is a high-molecular acidic polysaccharide (molecular weight: several tens thousands to several hundreds of thousands) which is mainly formed from uronic acid (D-mannuronic acid and L-guluronic acid) as a constituent saccharide and which is found in all brown algae as a cell wall substance. One constituent unit thereof has one carboxyl group. Potassium alginate is a salt formed through bonding potassium ions to the carboxyl groups of alginic acid.

The potassium alginate employed in the present invention is a low-molecule potassium alginate which has a weight average molecular weight, as determined through HPLC, of 60,000 or less, preferably 10,000 to 60,000, more preferably 20,000 to 60,000, even more preferably 20,000 to 50,000. Particularly when the potassium alginate is used in the form of a peroral liquid preparation, the viscosity of the liquid is preferably low, from the viewpoints of production thereof and favorable touch to the throat, sensation of sliminess, swallowability, and other considerations during drinking. Based on these viewpoints, the potassium alginate employed preferably has a low weight average molecular weight of 10,000 to 50,000, more preferably 10,000 to 40,000, even more preferably 10,000 to 30,000.

The potassium alginate of the present invention may be produced through a known method such as degradation under pressure and heat (JP-A-H06-7093) or enzymatic degradation (JP-A-H02-303468, JP-A-H03-94675, JP-A-H04-169189, JP-A-H06-245767, or JP-A-H06-217774). In one specific procedure, high-molecular-weight potassium alginate or alginic acid, serving as a raw material, is degraded under the conditions of, for example, pressure and heat, heating at ambient pressure, and in the presence of an enzyme, to thereby attain a molecular weight of interest. The thus-formed lower molecule product is optionally neutralized, dehydrated, and freeze-dried, to thereby yield potassium alginate. In the case of thermal degradation, molecular weight may be tuned by regulating pH at reaction, reaction temperature, reaction time, etc.

As described in the Examples hereinbelow, the thus-obtained potassium alginate of the present invention exhibits inhibitory effects on body weight increase, accumulation of visceral fat, and accumulation of liver lipid, which are associated with obesity promoted by intake of high-fat food, in the case where potassium alginate is ingested as aqueous solution (i.e., beverage) or as an ingredient incorporated into a meal.

Thus, the potassium alginate of the present invention can be employed in methods for preventing or ameliorating obesity, for inhibiting increase in body weight, for inhibiting accumulation of visceral fat, and for inhibiting accumulation of liver lipid, which are associated with obesity promoted by intake of high-fat food, which methods include administering potassium alginate to a subject (human or animal) in need thereof or having the subject take potassium alginate.

Namely, the potassium alginate may serve as an agent for preventing or ameliorating obesity, an agent for inhibiting accumulation of visceral fat, an agent for inhibiting accumulation of liver lipid, or an agent for preventing or ameliorating fatty liver (hereinafter collectively referred to as "agent for preventing or ameliorating obesity, etc."), which exhibits an inhibitory effects of body weight increase, accumulation of visceral fat and accumulation of liver lipid, which are associated with obesity promoted by intake of high-fat food.

The agent for preventing or ameliorating obesity may be pharmaceuticals, foods, feeds or the like to exhibit, per se, the effect for preventing or ameliorating obesity, for inhibiting increase of body weight, for inhibiting accumulation of visceral fat and for inhibiting accumulation of liver fat; or materials and preparations to be incorporated into the pharmaceuticals or the like. The foods may be a food such as beauty food, functional food, patient food, or food for specified health uses, with an optional label indicating a concept of prevention or amelioration of obesity, inhibition of accumulation of visceral fat, inhibition of accumulation of liver lipid, or prevention or amelioration of fatty liver.

As used herein, the term "high-fat food" refers to a food containing fat in a large amount, as defined by "The Lipid Reference Intakes for Japanese" (see "Dietary Reference Total Lipid Intakes," "Dietary Reference Saturated Fatty Acid Intakes," "Dietary Reference n-6 Fatty Acid Intakes," and "Dietary Reference Cholesterol Intakes," attached) as described in "The Dietary Reference Intakes for Japanese (2005 edition)" (Comments on "The Dietary Reference Intakes for Japanese (2005 edition)" on the homepage of the Ministry of Health, Labour and Welfare, issued on Nov. 22, 2004 by Health Policy Bureau, General Affairs Division, Office of Lifestyle-Related Disease Control, Nutrition Guidance Group <URL: http://www.mhlw.go.jp/houdou/2004/11/h1122-2.html#betu>). For example, the "high-fat food" has an energy ratio of total lipid to total intake energy of 30% or higher, preferably 40% or higher, more preferably 50% or higher, even more preferably 50 to 90%.

The total lipid energy ratio of the "high-fat food" may be calculated on the basis of one food, one meal, or meals consumed during the course of a day.

The pharmaceutical products containing potassium alginate may be, for example, peroral solid preparations such as tablet and granules, and peroral liquid preparations such as oral liquid and syrup.

A peroral solid preparation may be produced by mixing the potassium alginate of the present invention with a pharmaceutically acceptable carrier such as a diluent and, if required, a binder, a disintegrant, a lubricant, a colorant, a flavoring agent, a corrigent, etc., and forming the mixture into tablets, coated tablets, granules, powders, capsules, etc., through a conventional method. A peroral liquid preparation may be produced by mixing the potassium alginate with a flavoring agent, a buffer, a stabilizer, a corrigent, etc. and forming the mixture into peroral liquid, syrup, elixir, etc. through a routine method.

The amount of potassium alginate incorporated into each preparation is generally 0.01 to 100 wt. %, preferably 0.1 to 80 wt. %. More preferably, the amount is 1 to 50 wt. % for solid preparations, and 0.1 to 20 wt. % for liquid preparations.

A food and feed containing therein the potassium alginate of the present invention includes foods such as breads, confectionaries, jellied foods, dairy products, frozen foods, instant foods, starch-processing products, processed meat products and other processing products, drinks, soups, seasonings and nutritional supplement; feeds such as feeds for small animals including rabbits, rats and mice and pet foods for dogs, cats, birds, squirrels and the like.

The food or feed, if necessary, may optionally contain other component combined with the potassium alginate of the present invention. The other component preferably includes carriers acceptable in a food or feed field. Examples of the acceptable carries includes solvents, softeners, fats and oils, emulsifiers, preservatives, flavors, stabilizers, colorants, antioxidants, humectants, thickeners, gelatinizers, shape retaining agents, pH adjusters, seasonings and nutritional supplement products.

No particular limitation is imposed on a form of foods or feed. In addition to liquid, semi-solid and solid form, tablets, pills, capsules, liquids, syrups, powders, granules, or the like may be included, similar to a form of the peroral preparations.

The food or feed contains therein the potassium alginate of the present invention, depending on a form thereof, in an amount of 0.001 to 100 mass %, preferably 0.01 to 80 mass %, more preferably 0.1 to 50 mass % in term of dry weight. The drink preferably contains therein the potassium alginate of the present invention in an amount of 0.001 to 20 mass %, more preferably 0.1 to 10 mass %.

When the potassium alginate of the present invention is used for pharmaceuticals or foods, no particular limitation is imposed on the dose (effective amount taken by subject) thereof, so long as the target effect(s) can be attained. The daily dose (intake), which may vary depending on the condition, body weight, sex, or other factors of the subject, is preferably $\geq 0.001$ g/kg-body weight in terms of potassium alginate, more preferably 0.01 to 15.0 g/kg-body weight.

No particular limitation is imposed on the timing of administration of a variety of the preparation to a subject or having the subject take the preparation, and a timing of "during or before meals" is preferred. In the case where administration of the aforementioned preparation to a subject (or having the subject take the preparation) is carried out "between meals," the timing is preferably "before or while having a snack." Alternatively, the preparation may be administered or have taken as a snack.

No particular limitation is imposed on the frequency of ingestion or administration of a variety of the preparation per day, since it is highly safe. Administration or ingestion of one or more times per day is preferred. The frequency of ingestion or administration of the preparation per week is preferably 3 days or more, more preferably 5 days or more, even more preferably daily. The period of ingestion or administration of the preparation is preferably 2 weeks or longer, more preferably 4 weeks or longer.

No particular limitation is imposed on the subject to which the pharmaceutical products or foods of the present invention is administered or consumed, so long as the subject is in need of the agent. However, preferred target subjects include patients of nonalcoholic steatohepatitis (NASH); patients of obesity (BMI$\geq$25, and/or waist measurement of $\geq$85 cm (male) or $\geq$90 cm (female), and/or visceral fat area of $\geq$100 cm$^2$); patients of diabetes or impaired glucose tolerance (fasting blood glucose level of $\geq$110 mg/dL and/or OGTT 2-hour level of $\geq$140 mg/dL (WHO standards, 1998)); and patients of hyperlipidemea or impaired lipid metabolism (fasting blood neutral fat level of $\geq$150 mg/dL and/or HDL cholesterol level of <40 mg/dL).

Meanwhile, when a subject who is not at present in the state of obesity, diabetes or impaired glucose tolerance, or hyperlipidemia or impaired lipid metabolism (i.e., a healthy subject or a candidate) takes potassium alginate with a meal, particularly a high-fat food, the time of onset of obesity, diabetes, impaired glucose tolerance, hyperlipidemia, or impaired lipid metabolism, which will possibly occur in the future, is thought to be prolonged. Thus, healthy people may take potassium alginate for the purpose of prevention of such diseases or conditions.

EXAMPLES

Production Example (1)

Preparation of Potassium Alginate having a Weight Average Molecular Weight of about 50,000

A 5% solution of alginic acid (Duck Acid A (Lot. X-2702): product of Kibun Food Chemifa Co., Ltd.) was prepared, and the solution was heated at 100° C. for 45 minutes for degradation. The degradation product was neutralized with potassium hydroxide to a pH of 7. Subsequently, ethanol was added to the neutralization product so as to give 80% of ethanol content, and the formed precipitate was recovered through centrifugation (3000 rpm, 10 min) and dried, to thereby prepare a potassium alginate of interest.

The weight average molecular weight of the obtained potassium alginate, as measured through the below-described method, was found to be 52,163.

Production Example (2)

Preparation of Potassium Alginate having a Weight Average Molecular Weight of about 25,000

A 5% solution of alginic acid (Duck Acid A (Lot. X-2702): product of Kibun Food Chemifa Co., Ltd.) was prepared, and the solution was heated at 100° C. for 120 minutes for degradation. The degradation product was neutralized with potassium hydroxide to a pH of V. Subsequently, ethanol was added to the neutralization product so as to give 80% of ethanol content, and the formed precipitate was recovered through centrifugation (3000 rpm, 10 min) and dried, to thereby prepare a potassium alginate of interest.

The weight average molecular weight of the obtained potassium alginate, as measured through the below-described method, was found to be 25,801.

Determination of Average Molecular Weight of Alginic Acid or Salt thereof (Weight Average Molecular Weight Determination Method)

The weight average molecular weight of alginic acid (or a salt thereof) was determined through high-performance liquid chromatography (HPLC).

A portion (0.1 g) of alginic acid (or a salt thereof) was quantitatively dissolved in distilled water, to thereby provide a 0.1% solution thereof. The solution was employed as an HPLC analytical sample.

HPLC was performed under the following conditions. A calibration curve for the calculation of molecular weight was drawn by use of standard pullulan (Shodex STANDARD P-82, product of Showa Denko K.K.). An HPLC analytical sample (100 μL) was injected to an HPLC, and the weight average molecular weight of alginic acid (or a salt thereof) contained in the analytical sample was calculated from the obtained chromatographic chart.

<HPLC Operational Conditions>
Columns:
(1) Super AW-L (guard column) (product of Tosoh Corporation)
(2) TSK-GEL Super AW4000 (GPC column, exclusion limit of molecular weight: 4×10$^5$ PEO/DMF, length: 15 cm, inner diameter: 6 mm) (product of Tosoh Corporation)
(3) TSK-GEL Super AW2500 (GPC column, exclusion limit of molecular weight: 2×10$^3$ PEO/DMF, length: 15 cm, inner diameter: 6 mm) (product of Tosoh Corporation)

The aforementioned columns AW-L, AW4000, and AW2500 are linked in that order.

Column temperature: 40° C.
Detector: refractive index detector
Mobile phase: 0.2 mol/L aqueous sodium nitrate
Flow rate: 0.6 mL/min
Injection amount: 100 μL Test Example 1

Effect of Potassium Alginate on Anti-Obesity 1-1 Test Samples
The potassium alginate produced in Production Example 1 (hereinafter referred to as "K alginate (mol. wt. 50,000)") and the potassium alginate produced in Production Example 2 (hereinafter referred to as "K alginate (mol. wt. 25,000)") were employed as potassium alginate samples.

1-2 Test Groups
K alginate intake was realized through the following two methods: (1) dissolving K alginate in purified water and feeding the aqueous solution (feeding water), and (2) incorporating K alginate into a meal (feeding meal).
The following six groups were subjected to a breed test (N=10 in each group).
In the Test Examples, the term "high-fat food" refers to a food containing fat in a large amount, with reference to the aforementioned "The Dietary Reference Intakes for Japanese (2005 edition), Dietary Reference Total Lipid Intakes" (lipid energy ratio: 52 to 53%), and the term "low-fat food" refers to a food containing fat in a small amount, with reference to the aforementioned "The Dietary Reference Intakes for Japanese (2005 edition), Dietary Reference Total Lipid Intakes" (lipid energy ratio: 12%).

TABLE 1

| Test groups | | Meal feeding (test food) | Water feeding (test water) |
|---|---|---|---|
| 1 | low-fat food | low-fat food | purified water |
| 2 | high-fat food | high-fat food | purified water |
| 3 | K alginate (mol. wt.: 25,000) in water (5%) | high-fat food | K alginate (mol. wt.: 25,000) 5% aq. solution |
| 4 | K alginate (mol. wt.: 25,000) in meal (5%) | high-fat food + K alginate (mol. wt.: 25,000) (5%) | purified water |
| 5 | K alginate (mol. wt.: 50,000) in water (5%) | high-fat food | K alginate (mol. wt.: 50,000) 5% aq. solution |
| 6 | K alginate (mol. wt.: 50,000) in meal (5%) | high-fat food + K alginate (mol. wt.: 50,000)(5%) | purified water |

1-3 Feeding Meal (Test Food) Composition
Table 2 shows the compositions of the test foods given to each of the Test groups.

TABLE 2

Compositions of test foods (content: %)

| Ingredients | Test food for Test group 1 low-fat food | Test food for Test groups 2, 3, and 5 high-fat food | Test food for Test group 4 high-fat food + K alginate (mol. wt.: 25,000) (5%) | Test food for Test group 6 high-fat food + K alginate (mol. wt.: 50,000) (5%) |
|---|---|---|---|---|
| Corn oil | 5 | 25 | 25 | 25 |
| Lard | — | 5 | 5 | 5 |
| K alginate (mol. wt.: 25,000) | — | — | 5 | — |
| K alginate (mol. wt.: 50,000) | — | — | — | 5 |
| Sucrose | — | 13 | 13 | 13 |
| Casein | 20 | 20 | 20 | 20 |
| Cellulose | 4 | 4 | 4 | 4 |
| AIN76 mineral mixture | 3.5 | 3.5 | 3.5 | 3.5 |
| AIN76 vitamin mixture | 1 | 1 | 1 | 1 |
| α-Potato starch | 66.5 | 28.5 | 23.5 | 23.5 |
| Total | 100 | 100 | 100 | 100 |
| Lipid energy ratio (%) | 11.5 | 52.3 | 53.4 | 53.4 |

In the test foods, corn oil, lard, casein, cellulose, AIN76 mineral mixture, AIN76 vitamin mixture, and α-potato starch were products of Oriental Yeast Co., Ltd., and sucrose was fine granules of sucrose (special grade) and a product of Wako Pure Chemical Industries, Ltd.

1-4 Fed Water (Test Water) Composition
A 5 w/w % aqueous solution of K alginate (mol. wt.: 25,000) and that of K alginate (mol. wt.: 50,000) were prepared on the day when the test water was applied. These two aqueous solutions have so low viscosity that they can be fed by means of a water feed bottle generally employed in breeding animals. Thus, test animals can readily take the test water as tap water.

1-5 Test Animal and Breeding Conditions
7-Week-old male C57BL/6J Jcl mice (purchased from Clea Japan) were bred for one week, while maintained on a common food (CE-2: moisture 9.3%, crude protein 25.1%, crude fat 4.8%, crude fiber 4.2%, crude ash 6.7%, and NFE 50.0%, product of Clea Japan). After breeding, at the age of 8 weeks, the mice were weighed and classified into six Test groups so that the initial body weights of these groups were substantially equal.

After classification, feeding of meal and water (shown in Table 1) was carried out for the test to week 18. The mice were maintained on food and water ad libitum, where Roden Cafe was used as a base of the food, and water was supplied by means of a water feed bottle.

Energy intake was calculated from the following unit values: lipid (9.0 kcal/g), sugar (4.0 kcal/g), protein (4.0 kcal/g), and potassium alginate (2 kcal/g) (see Note 1). (Note 1) Unit calorie value of potassium alginate In the notifications of the Ministry of Health, Labour and Welfare (Feb. 17, 2003); "Partial Revision of 'Practice of Nutrition Labeling Standards'" (Issue No. 0217001) and "Partial Revision of 'Method for Analysis of nutrients in Nutrition Labeling Standards' (Issue No. 0217002), energy conversion factors of various dietary fibers are described. However, potassium alginate, which was employed in the test of the invention, is not described in these notifications. According to the above notifications of the Ministry of Health, Labour and Welfare, the energy conversion factor for a dietary fiber which is not described in these notifications is provisionally determined as 2 kcal/g. Thus, in the present invention, energy calculation was carried out with an energy conversion factor of potassium alginate of 2 kcal/g.

1-6 Removal of the Visceral Fat and Livers for Measuring Visceral Fat Weight and Liver Lipid On the final day of the test, mice were maintained on food and water ad libitum just before anatomization. Under anesthetization with ether, the mice were immediately subjected to peritoneotomy and sacrificed through exsanguination via the abdominal vena cava. Immediately thereafter, the liver was removed from each mouse, and the weight of the liver was measured. The thus-obtained liver was quickly frozen in liquid nitrogen for the measurement of liver lipid. Furthermore, visceral fat (periepididymal, perinephric, retroperitoneal, and mesenteric) was removed and weighed. The sum of the fat weights was employed as the amount of visceral fat.

The obtained liver was stored in a freezer at −80° C. from completion of anatomization to measurement of liver lipid.

1-7 Data Analysis and Statistical Test

During breeding, two mice were severely and widely injured by fighting, and the injuries were observed until the final test day (injury of about ⅕ or more of the body surface visually observed, presence of muscle exposure, continuous from breeding week 10 or 11 to breeding week 18 (final test day)). Thus, the two mice were excluded from data analysis.

The body weight, and the amounts of visceral fat and liver lipid were measured, and average± standard error (S.E.) values were calculated. Statistical testing was performed through Fisher's PLSD test.

1-8 Results 1-8 (1) Body Weight

Tables 3 and 4 show the body weights of mice before the test, after breeding week 4, breeding week 8, breeding week 12, and breeding week 18.

Test group 3 (K alginate, mol. wt.: 25,000, 5% in water) and Test group 5 (K alginate, mol. wt.: 50,000, 5% in water) exhibited significantly lower body weights after breeding week 4, as compared with Test group 2 (high-fat food), indicating suppression of increase in body weight. During the test period, Test groups 3 and 5 exhibited body weights not lower than the body weight of Test group 1 (low-fat food). Therefore, growth of mice in Test groups 3 and 5 was not thought to be inhibited.

Test group 4 (K alginate, mol. wt.: 25,000, 5% in meal) and Test group 6 (K alginate, mol. wt.: 50,000, 5% in meal) exhibited significantly lower body weights after breeding week 12, as compared with Test group 2 (high-fat food), indicating suppression of increase in body weight. During the test period, Test groups 4 and 6 exhibited body weights not lower than the body weight of Test group 1 (low-fat food). Therefore, growth of mice in Test groups 4 and 6 was not thought to be inhibited.

Through the above test, potassium alginate is thought to exhibit excellent inhibitory effect on body weight increase, which would otherwise be promoted by intake of high-fat food, when potassium alginate is in the form of aqueous solution or has been incorporated into a meal.

TABLE 3

Body weights (before test, week 4, and week 8)

| | Test groups | Before test (g) | Week 4 (g) | | Week 8 (g) | |
|---|---|---|---|---|---|---|
| 1 | low-fat food | 21.12 ± 0.12 | 26.79 ± 0.33 | *** | 31.33 ± 0.43 | *** |
| 2 | high-fat food | 21.21 ± 0.09 | 30.07 ± 0.46 | — | 37.61 ± 0.72 | — |
| 3 | K alginate (mol. wt.: 25,000) in water (5%) | 21.15 ± 0.10 | 28.48 ± 0.24 | ** | 32.78 ± 0.66 | *** |
| 4 | K alginate (mol. wt.: 25,000) in meal (5%) | 21.27 ± 0.13 | 29.45 ± 0.34 | N.S. | 36.62 ± 0.41 | N.S. |
| 5 | K alginate (mol. wt.: 50,000) in water (5%) | 21.13 ± 0.12 | 28.35 ± 0.38 | ** | 33.84 ± 0.83 | *** |
| 6 | K alginate (mol. wt.: 50,000) in meal (5%) | 21.43 ± 0.13 | 29.56 ± 0.40 | N.S | 36.76 ± 0.98 | N.S |

Each of values indicates Av. ± S.E., Fisher's PLSD test was performed with respect to Test group 2 (high-fat food)
( $P < 0.01$, * $P < 0.001$)

TABLE 4

Body weights (week 12 and week 18)

| | Test groups | Week 12 (g) | | Week 18 (g) | |
|---|---|---|---|---|---|
| 1 | low-fat food | 33.63 ± 0.46 | *** | 36.10 ± 0.60 | *** |
| 2 | high-fat food | 42.28 ± 1.10 | — | 46.66 ± 0.98 | — |
| 3 | K alginate (mol. wt.: 25,000) in water (5%) | 35.45 ± 0.68 | *** | 39.34 ± 0.77 | *** |
| 4 | K alginate (mol. wt.: 25,000) in meal (5%) | 39.69 ± 0.58 | * | 42.26 ± 0.87 | ** |
| 5 | K alginate (mol. wt.: 50,000) in water (5%) | 36.85 ± 1.14 | *** | 39.66 ± 1.53 | *** |
| 6 | K alginate (mol. wt.: 50,000) in meal (5%) | 39.44 ± 1.09 | * | 42.35 ± 1.33 | ** |

Each of values indicates Av. ± S.E., Fisher's PLSD test was performed with respect to Test group 2 (high-fat food)
(* $P < 0.05$,  $P < 0.01$, * $P < 0.001$)

Table 5 shows the total calorie intake (during 18 test weeks) and feed efficiency (body weight increase (18 weeks)/total calorie intake). The amounts of test food intake and test water intake were measured cage by cage. Thus, the total calorie intake was calculated through averaging two cages of each group.

While the high-fat food group exhibited a total calorie intake of 1,534 kcal/mouse, the potassium alginate intake groups exhibited a total calorie intake of 1,404 to 1,528 kcal/mouse; i.e., potassium alginate intake groups exhibited a cumulative calorie intake lower than that of the high-fat food group. However, although the high-fat food group exhibited a feed efficiency of 16.6 mg/kcal/mouse, the potassium alginate intake groups exhibited a low feed efficiency of 12.7 to 14.6 mg/kcal/mouse. Thus, when the same amount calories is taken in, the potassium alginate intake groups are thought to exhibit a smaller increase in body weight, as compared with the high-fat food group, and intake of potassium alginate is thought to inhibit body weight increase.

TABLE 5

Total calorie intake of test food and water and feed efficiency

| | Test groups | Total calorie intake of test food and water (kcal/mouse) | Feed efficiency; 18-weeks bodyweight increase (mg)/total calorie intake (kcal/mouse) |
|---|---|---|---|
| 1 | low-fat food | 1,605 | 9.3 |
| 2 | high-fat food | 1,534 | 16.6 |
| 3 | K alginate (mol. wt.: 25,000) in water (5%) | 1,404 | 13.0 |
| 4 | K alginate (mol. wt.: 25,000) in meal (5%) | 1,436 | 14.6 |
| 5 | K alginate (mol. wt.: 50,000) in water (5%) | 1,456 | 12.7 |
| 6 | K alginate (mol. wt.: 50,000) in meal (5%) | 1,528 | 13.7 |

1-8 (2) Visceral Fat Amount

Table 6 shows visceral fat amounts of the test groups.

Test group 2 (high-fat food) exhibited a significantly larger visceral fat amount, as compared with Test group 1 (low-fat food), indicating accumulation of visceral fat.

Test group 3 (K alginate, mol. wt.: 25,000, 5% in water), Test group 5 (K alginate, mol. wt.: 50,000, 5% in water), and Test group 6 (K alginate, mol. wt.: 50,000, 5% in meal) exhibited a significantly smaller visceral fat amount, as compared with Test group 2 (high-fat food), indicating inhibition of accumulation of visceral fat.

Test group 4 (K alginate, mol. wt.: 25,000, 5% in meal) exhibited a slightly smaller visceral fat (P=0.0695), as compared with Test group 2 (high-fat food), indicating inhibition of accumulation of visceral fat.

Through the above test, potassium alginate is thought to exhibit excellent inhibitory effect on accumulation of visceral fat, which would otherwise be promoted by intake of high-fat food, when potassium alginate is in the form of aqueous solution or has been incorporated into a meal.

TABLE 6

Visceral fat amount

| | Test groups | Visceral fat amount (g) | |
|---|---|---|---|
| 1 | low-fat food | 2.8599 ± 0.1259 | *** |
| 2 | high-fat food | 4.9539 ± 0.1386 | — |
| 3 | K alginate (mol. wt.: 25,000) in water (5%) | 3.4313 ± 0.2084 | *** |
| 4 | K alginate (mol. wt.: 25,000) in meal (5%) | 4.2154 ± 0.2144 | P = 0.0695 |
| 5 | K alginate (mol. wt.: 50,000) in water (5%) | 3.5511 ± 0.4010 | *** |
| 6 | K alginate (mol. wt.: 50,000) in meal (5%) | 3.8556 ± 0.3561 | ** |

Each of values indicates Av. ± S.E., Fisher's PLSD test was performed with respect to Test group 2 (high-fat food)
( P < 0.01, * P < 0.001)

Test Example 2

Inhibitory Effect of Potassium Alginate on Accumulation of Liver Lipid

The livers obtained in Test Example 1 were used. Specifically, each liver which had been frozen at −80° C. was thawed at room temperature, and a portion (0.25 g) taken from the liver was subjected to liver lipid extraction through the Folch method. The amount of lipid in 1 g of liver was calculated. The results are shown in Table 7.

Test group 2 (high-fat food) exhibited a significantly larger liver lipid amount, as compared with Test group 1 (low-fat food), indicating accumulation of fat in the liver (fatty liver).

In contrast, Test group 3 (K alginate, mol. wt.: 25,000, 5% in water), Test group 4 (K alginate, mol. wt.: 25,000, 5% in meal), Test group 5 (K alginate, mol. wt.: 50,000, 5% in water), and Test group 6 (K alginate, mol. wt.: 50,000, 5% in meal) exhibited a significantly smaller liver lipid amount, as compared with Test group 2 (high-fat food), indicating inhibition of accumulation of lipid in the liver.

Through the above test, potassium alginate is thought to exhibit excellent inhibitory effect on accumulation of liver lipid, which would otherwise be promoted by intake of high-fat food, when potassium alginate is in the form of aqueous solution or has been incorporated into a meal.

TABLE 7

Liver lipid amount

| | Test groups | Liver lipid amount (g/1 g-liver) | |
|---|---|---|---|
| 1 | low-fat food | 0.0892 ± 0.0085 | *** |
| 2 | high-fat food | 0.1451 ± 0.0096 | — |
| 3 | K alginate (mol. wt.: 25,000) in water (5%) | 0.0971 ± 0.0054 | *** |
| 4 | K alginate (mol. wt.: 25,000) in meal (5%) | 0.1021 ± 0.0066 | *** |
| 5 | K alginate (mol. wt.: 50,000) in water (5%) | 0.1060 ± 0.0077 | ** |
| 6 | K alginate (mol. wt.: 50,000) in meal (5%) | 0.0916 ± 0.0080 | *** |

Each of values indicates Av. ± S.E., Fisher's PLSD test was performed with respect to Test group 2 (high-fat food)
( P < 0.01, * P < 0.001)

What is claimed is:

1. A method for ameliorating obesity, the method comprising administering potassium alginate to a subject in need thereof or having the subject take potassium alginate for a period of at least 4 weeks.

2. The method of claim 1, wherein ameliorating obesity comprises reducing the accumulation of visceral fat.

3. The method of claim 1, wherein ameliorating obesity comprises reducing the accumulation of liver lipids.

4. The method of claim 1, wherein ameliorating obesity comprises ameliorating fatty liver.

5. The method for ameliorating obesity according to claim 1, wherein potassium alginate has a weight average molecular weight of 10,000 to 60,000.

6. The method of ameliorating obesity according to claim 1, wherein potassium alginate has a weight average molecular weight of 20,000 to 50,000.

7. The method of ameliorating obesity according to claim 6, comprising administering potassium alginate to a subject in need thereof or having the subject take potassium alginate at least once per day.

8. The method of ameliorating obesity according to claim 1, comprising administering potassium alginate to a subject in need thereof or having the subject take potassium alginate for a period of at least 8 weeks.

9. The method of ameliorating obesity according to claim 8, wherein potassium alginate has a weight average molecular weight of 20,000 to 50,000.

10. The method of ameliorating obesity according to claim 9, comprising administering potassium alginate to a subject in need thereof or having the subject take potassium alginate at least once per day.

11. The method of ameliorating obesity according to claim 1, comprising administering potassium alginate to a subject in need thereof or having the subject take potassium alginate for a period of at least 12 weeks.

12. The method of ameliorating obesity according to claim 11, wherein potassium alginate has a weight average molecular weight of 20,000 to 50,000.

13. The method of ameliorating obesity according to claim 12, comprising administering potassium alginate to a subject in need thereof or having the subject take potassium alginate at least once per day.

* * * * *